United States Patent
Seltzer (10) Patent No.: US 6,690,462 B2
(45) Date of Patent: Feb. 10, 2004

(54) CALIBRATION SCHEME FOR CONTINUOUS MONITORING OF MERCURY EMISSIONS FROM STATIONARY SOURCES BY PLASMA EMISSION SPECTROMETRY

(75) Inventor: Michael D. Seltzer, Ridgecrest, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/005,822

(22) Filed: Dec. 5, 2001

(65) Prior Publication Data
US 2003/0103206 A1 Jun. 5, 2003

(51) Int. Cl.⁷ .............................. G01J 3/30; G12B 13/00
(52) U.S. Cl. ..................................... 356/316; 250/252.1
(58) Field of Search ...................... 356/316; 250/252.1; 73/1.01–1.02

(56) References Cited

U.S. PATENT DOCUMENTS

| | | | | |
|---|---|---|---|---|
| 5,526,110 A | * | 6/1996 | Braymen ..................... | 356/316 |
| 5,596,405 A | | 1/1997 | Seltzer et al. | |
| 5,679,957 A | * | 10/1997 | Durham et al. ............. | 250/373 |
| 5,750,992 A | * | 5/1998 | Van Pelt et al. ............ | 250/372 |
| 5,777,734 A | * | 7/1998 | Flower et al. ............... | 356/341 |
| 5,834,656 A | | 11/1998 | Seltzer | |
| 5,908,566 A | | 6/1999 | Seltzer | |
| 5,986,757 A | | 11/1999 | Seltzer | |

FOREIGN PATENT DOCUMENTS

DE 195 06 875 * 10/1996 ............ G01N/1/22

OTHER PUBLICATIONS

Seltzer, M. D., and Meyer, G. A., Inductively Coupled Argon Plasma Continuous Emissions Monitor for Hazardous Air Pollutant Metals, Environmental Science and Technology, 1997, pp. 2665–2672, vol. 31, Advance ACS Abstracts.

Seltzer, M. D., Performance Testing of a Multimetals Continuous Emissions Monitor, Journal of the Air and Waste Management Association, 2000, pp. 1010–1016, vol. 50.

Baldwin, D. P. et al., Testing of Continuous Sampling Air–ICP and Mercury Systems as Continuous Emission Monitors at the Diagnostic Instrumentation and Analysis Laboratory, Sep. 18–26 2000, pp. 25.

* cited by examiner

Primary Examiner—F. L. Evans
Assistant Examiner—Kara Geisel
(74) Attorney, Agent, or Firm—Laura R. Foster; Anthony J. Serventi (57) ABSTRACT

The disclosed invention relates to a calibration method, system and apparatus for a multimetals continuous emissions monitor system (hereinafter "multimetals CEMS"). More specifically, this invention relates to a calibration scheme for continuous monitoring of mercury emissions from stationary sources by plasma emission spectrometry. A source of mercury vapor, preferably a mercury permeation tube, entrains mercury vapor into a constant flow of carrier air. The carrier air mixes with a constant flow of diluent air in an aerosol mixer. The mixer is operably coupled to the analyzer. A gaseous mixture having a calibration mercury concentration flows from the mixer into the analyzer at a constant rate. A graph having coordinates of analyzer signal intensity and mercury concentration is used to plot the calibration scheme. A first signal intensity generated by the analyzer in response to the calibration mercury concentration is used for the first plot on the graph. A second signal intensity generated by the analyzer in response to a blank having zero mercury concentration is used as the second plot on the graph. A linear relationship between the analyzer signal intensity and the mercury concentration on the graph is established from the first plot and the second plot. The slope intercept and slope are used to create a mathematical relationship between the analyzer signal intensity and the mercury concentration. This enables the analyzer to be calibrated by inserting a known mercury concentration into the analyzer and adjusting the signal intensity to conform to the signal intensity calculated from the graph or mathematical relationship.

26 Claims, 5 Drawing Sheets

CALIBRATION SCHEME FOR CONTINUOUS MONITORING OF MERCURY EMISSIONS FROM STATIONARY SOURCES BY PLASMA EMISSION SPECTROMETRY

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND OF THE INVENTION

1. Field of the Invention

This invention relates to a calibration scheme for a multimetals continuous emissions monitor system (hereinafter "multimetals CEMS"). More specifically, this invention relates to a calibration scheme for continuous monitoring of mercury emissions from stationary sources by plasma emission spectrometry.

2. Description of the Prior Art

Almost exclusively, analyzers or continuous emission monitors for gaseous pollutants such as carbon monoxide, nitrogen oxides, hydrogen chloride, etc., are calibrated using commercially-available gas mixtures that contain precise, certified amounts of the pollutant species in question These mixtures are readily prepared by commercial vendors and then certified by suitable analytical methods. The certification is most often "traceable" to reference standards provided by the National Institutes of Standards and Technology (formerly the National Bureau of Standards). The continuous monitoring of hazardous air pollutant metals is an emerging technology that presents a number of unique technological challenges. Unlike the gaseous air pollutant described above, there are no sources for "standard" gas mixtures containing "known" amounts of metal pollutants. Metal elements exist primarily in the solid phase except at extremely high temperatures and therefore do not lend themselves to mixture and containment in the gaseous state. The one exception is mercury, which can exist as both a liquid and gas at room temperature. There have been some efforts in the commercial arena to prepare gaseous mixtures of mercury vapor (contained in cylinders) potentially useful in applications similar to that described in the present invention disclosure. However, those devices are most directly applicable for calibrating batch-sampling mercury analyzers exclusively dedicated to the detection of mercury. Batch-sampling mercury analyzers do not continuously measure mercury in sample gas. Rather, batch-sampling mercury analyzers accumulate a mercury sample over a period of time before measuring the sample. These calibrating batch-sampling mercury analyzers use analytical methodologies that are distinctly different from those employed by the multimetals CEMS. Thus far, the developers of this product have been able to certify the contents of the gas cylinder in terms of mercury concentration, but at present, are unable to provide certification of the mercury concentration of the delivered gas stream.

For the specific multimetals CEMS described above, a calibration method has been developed in which dry aerosols of known metal composition and concentration can be generated and used in lieu of unavailable gaseous calibration mixtures. This calibration method is briefly summarized here, but for a more detailed discussion please see Seltzer, M. D. and Meyer, G. A. *Inductively Coupled Argon Plasma Continuous Emissions Monitor for Hazardous Air Pollutant Metals* Environmental Science and Technology, Vol. 31, (1997), pp. 2665–2672, which is incorporated herein by reference. Aqueous solutions containing known amounts of dissolved metal salts, primarily metal nitrates, are delivered at a fixed rate of 1.5 mL/min into a COTS device known as an ultrasonic nebulizer. The ultrasonic nebulizer creates a fine, liquid aerosol from these solutions that is entrained by a carrier gas flow of 1.1 L/min through a desolvation system. The desolvation system consists of a heater that raises the temperature of the liquid aerosol carrier air mixture to 140° C. that effectively evaporates the liquid water and produces water vapor. Following evaporation of the water from the liquid aerosol droplets, the dissolved metal salt component of each aerosol droplet coalesces into a solid metal salt particle. The metal salt particulate/water vapor/carrier air stream then passes through a thermoelectric cooler that reduces the temperature of the mixture to 4° C. and effectively condenses and removes the water vapor component. Exiting the ultrasonic nebulizer device is a carrier air stream containing suspended metal salt particles. Through systematic characterization of the ultrasonic nebulizer's efficiency, the output of the nebulizer, in terms of micrograms of metal per minute, is precisely known. Therefore, the process described above is extremely useful for calibration of the multi metal CEMS. The validity of the calibration scheme has been established through rigorous performance testing in which the accuracy of the multimetals CEMS was verified in comparison to an EPA-approved test method, as described in Seltzer, M. D. *Performance Testing of a Multimetals Continuous Emissions Monitor*, Journal of the Air and Waste Management Association, Vol. 50 (2000), pp. 1010–1016, which is incorporated herein by reference.

The method described above for generating calibration aerosols works extremely well for virtually all metals except mercury. Since this method employs aqueous solutions of dissolved metal salts as starting materials to generate dry aerosols of the metals in question, suitable metal salts must be available for all metals. The soluble salts of mercury, in particular mercuric nitrate, thermally decompose at relatively low temperatures (ca. 100° C.) and therefore are not very stable in comparison to the salts of the other heavy metals, i.e., Pb, Cd, As, Be, Cr, etc. Also, the mercuric nitrate salt particles have a unique tendency to deposit or accumulate within the ultrasonic nebulizer and within various components of the multimetals CEMS sampling system and sampling interface. Because of their poor thermal stability, the mercuric nitrate salt particles tend to spontaneously decompose and produce elemental mercury vapor. The spurious release of the mercury vapor has the undesired effect of confounding the mercury calibration process, and later, during actual monitoring procedures, can produce "ghost" signals or "memory" effects that can adversely affect measurement accuracy.

The use of a mercury permeation device to calibrate an apparatus designed to measure airborne mercury in combustor exhaust gases is described in Baldwin, D. P. et al. *Testing of Continuous Sampling Air-ICP and Mercury Systems as Continuous Emission Monitors at the Diagnostic Instrumentation and Analysis Laboratory*, Report IS-5144, Sep. 18–26, 2000. The technique described therein involves a permeation device to calibrate a dedicated mercury analyzer that measures mercury only, using absorption spectrometry. The method, system and apparatus of the present invention, described below, utilizes a permeation device to calibrate an instrument for mercury detection. However, the instrument of the present invention measures all metal elements, including mercury, using emission spectrometry, rather than absorption spectrometry.

Accordingly, a method for producing a mercury calibration stream is required that will provide precisely-known quantities of mercury in a thermally-stable form that will not persist in various components of the multimetals CEMS instrument after flow of the calibration stream is deliberately terminated.

SUMMARY OF THE INVENTION

A preferred embodiment of the present invention addresses the need for a simple and reliable means of generating and introducing a known concentration of mercury for calibration of analytical instrumentation used for monitoring the emission of mercury and other hazardous air pollutant metals from waste incinerators and other stationary sources of air pollutants. The calibration material should be in the same physical form, i.e., elemental vapor, as the anticipated pollutant emission from the subject stationary source in order that the amplitude and character of the response of the monitor or analyzer be similar for both the calibration material and actual pollutant species. Since extensive test evidence indicates that stationary sources including waste incinerators and coal-burning power plants emit mercury almost exclusively in the elemental vapor phase, a calibration material consisting of elemental mercury vapor is most appropriate for reasons expressed above.

A multimetals CEMS is designed to acquire and analyze a gaseous sample stream from the stationary source in question, and determine the concentrations of various metals that are categorized as hazardous air pollutants by the U.S. EPA and other regulatory agencies. See U.S. Pat. No. 5,596,405, *Method and Apparatus for the Continuous Emissions Monitoring of Toxic Airborne Metals*, issued to Seltzer et al, Jan. 21, 1997, U.S. Pat. No. 5,834,656, *Sampling Interface for Continuous Monitoring of Emissions* issued to Seltzer on Nov. 10, 1998, U.S. Pat. No. 5,908,566, *Modified Plasma Torch Design for Introducing Sample Air into Inductively Coupled Argon Plasma* issued to Seltzer on Jun. 1, 1999 and U.S. Pat. No. 5,986,757, *Correction of Spectral Interferences Arising from CN Emission in Continuous Air Monitoring using Inductively Coupled Plasma Atomic Emission Spectroscopy* issued to Seltzer on Nov. 16, 1999, all of which are incorporated herein by reference. During the analysis process, the analytical instrumentation that comprises the multimetals CEMS measures signal intensities from the individual metal elements present in the gaseous sample stream. In order to provide metal concentration values that correspond to these signal intensities, the signal response of the instrument must first be calibrated using "standard" gaseous samples containing "known" amounts of each individual metal element. By measuring a series of "standard" samples that contain increasing amounts of a specific metal, and recording the corresponding signal intensities for each "standard", a linear relationship can be established between signal intensity and metal concentration. Typically, the calibration procedure involves measurement of a blank or "Zero" standard, and a high concentration or "Span" standard. The resulting linear relationship forms the basis of quantitative analysis in which samples of "unknown" concentration are measured, their corresponding signal intensities recorded, and actual metal concentrations calculated.

In a preferred embodiment of the present invention, a method of calibration for detection of mercury pollutants by a continuous emissions analyzer is described. First, a mercury permeation tube is placed inside the constant temperature chamber and a constant flow rate of carrier air is introduced. Next, the mercury vapor/carrier air stream is introduced into a mixing device along with a constant flow of diluent air to achieve a total flow, which is the combination of the constant flow rates of the carrier air and the diluent air. The resulting calibration gas mixture contains a mercury concentration calculated by dividing the output rate of the mercury permeation tube by the total flow. Next, the calibration gas mixture is introduced into the multimetals CEMS or other analyzer device and the corresponding signal response is recorded. Next, calibration gas mixtures containing other "known" amounts of mercury vapor can be introduced and measured in the same manner. Next, a linear relationship is established between signal intensity and mercury concentration. Finally, the calibration gas mixture can be reintroduced at a later time to confirm the stability of the original calibration.

A calibration system for detection of mercury pollutants by a continuous emissions analyzer, preferably a plasma emissions spectrometer. A constant temperature chamber houses a mercury permeation tube. The mercury permeation tube has a known output rate and is set inside the chamber to entrain mercury vapor into carrier air. The carrier air flows into the chamber at a constant rate from a mass flow controller or other means for controlling air flow. The mercury entrained carrier air flows from the chamber and into an aerosol mixer operably coupled to the chamber. In a preferred embodiment, a 3-way solenoid valve is set between chamber and the mixer. The valve may be set to direct the mercury entrained carrier air into the mixer or the valve may be set to direct the mercury entrained carrier air into a trap, such as an activated charcoal trap, to prevent the escape of pollutants into the atmosphere. The mixer is operably coupled to the analyzer. A means for controlling diluent air is operably coupled to the mixer and introduces diluent air into said mixer at a constant rate. A gaseous mixture having a calibration mercury concentration flows from the mixer into the analyzer at a constant rate. A graph having coordinates of analyzer signal intensity and mercury concentration is used to plot the calibration scheme. A first signal intensity generated by the analyzer in response to the calibration mercury concentration is used for the first plot on the graph. A second signal intensity generated by the analyzer in response to a blank having zero mercury concentration is used as the second plot on the graph. However, any known mercury concentration may be used as the source of the second plot, but zero mercury concentration is most preferred because it provides the slope intercept. A linear relationship between the analyzer signal intensity and the mercury concentration on the graph is established from the first plot and the second plot. The slope intercept and slope are used to create a mathematical relationship between the analyzer signal intensity and the mercury concentration. This enables the analyzer to be calibrated by inserting a known mercury concentration into the analyzer and adjusting the signal intensity to conform to the signal intensity calculated from the graph or mathematical relationship.

One object of a preferred embodiment of the present invention is to provide a novel calibration scheme for detection of mercury pollutants by a multimetals continuous emissions monitor.

Another object of a preferred embodiment of the present invention is to provide a calibration apparatus which employs COTS components including a mercury permeation tube and constant temperature chamber and uses these components in a unique application.

Another object of a preferred embodiment of the present invention is to provide a calibration apparatus which employs a mercury permeation tube to generate mercury vapor at a constant, known output rate to be used as a calibration standard for a specific process.

Another object of a preferred embodiment of the present invention is to provide a calibration apparatus in which the mercury vapor calibration standard is in the same physical form as the mercury pollutant to be detected.

Another object of a preferred embodiment of the present invention is to provide a calibration scheme that is completely compatible for use in conjunction with a multimetals continuous emissions monitor.

DETAILED DESCRIPTION OF THE INVENTION

Figure 1:
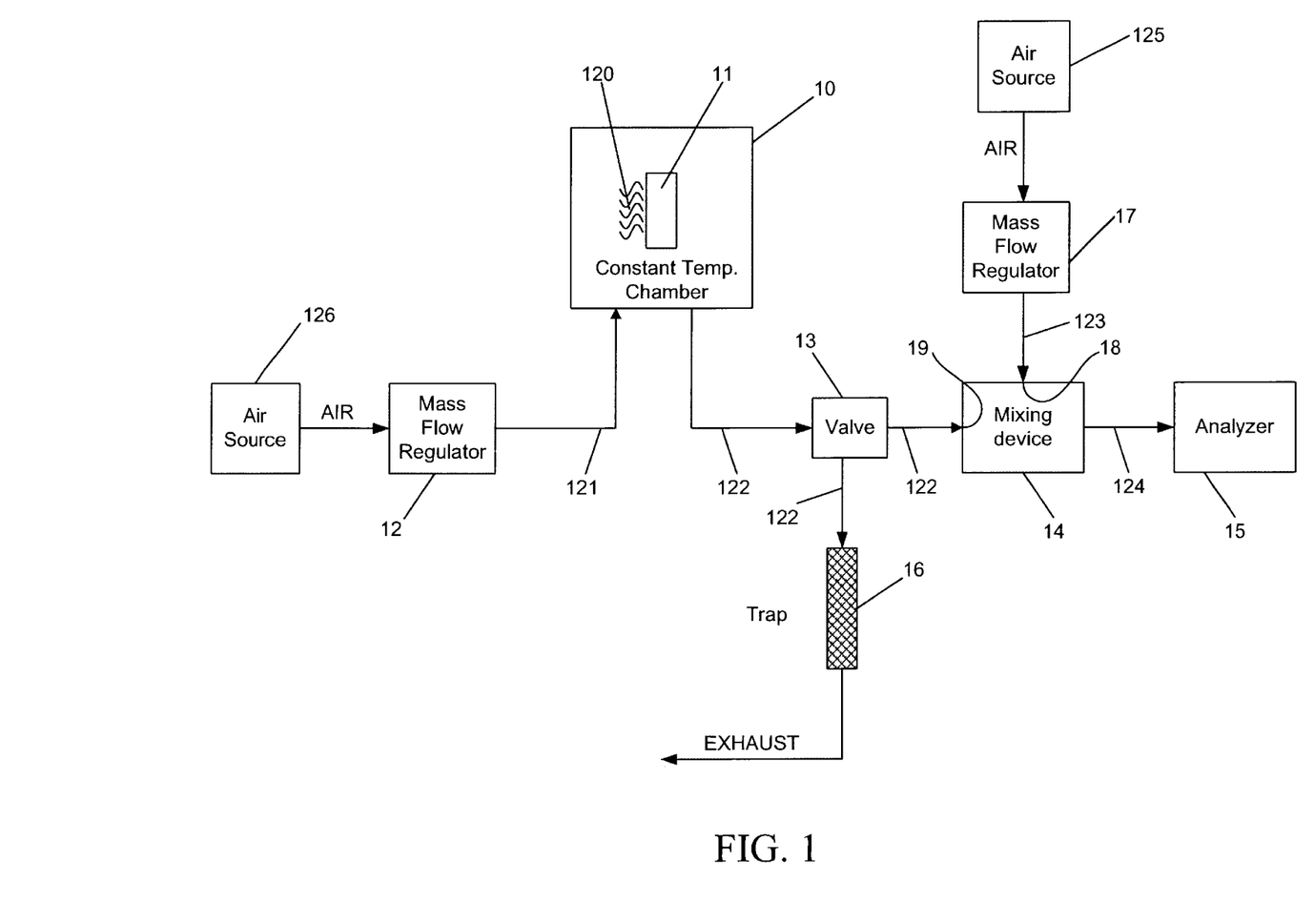
FIG. 1 is a schematic drawing of a mercury calibration apparatus for multimetals CEMS for a preferred embodiment of the present invention.
Figure 5:
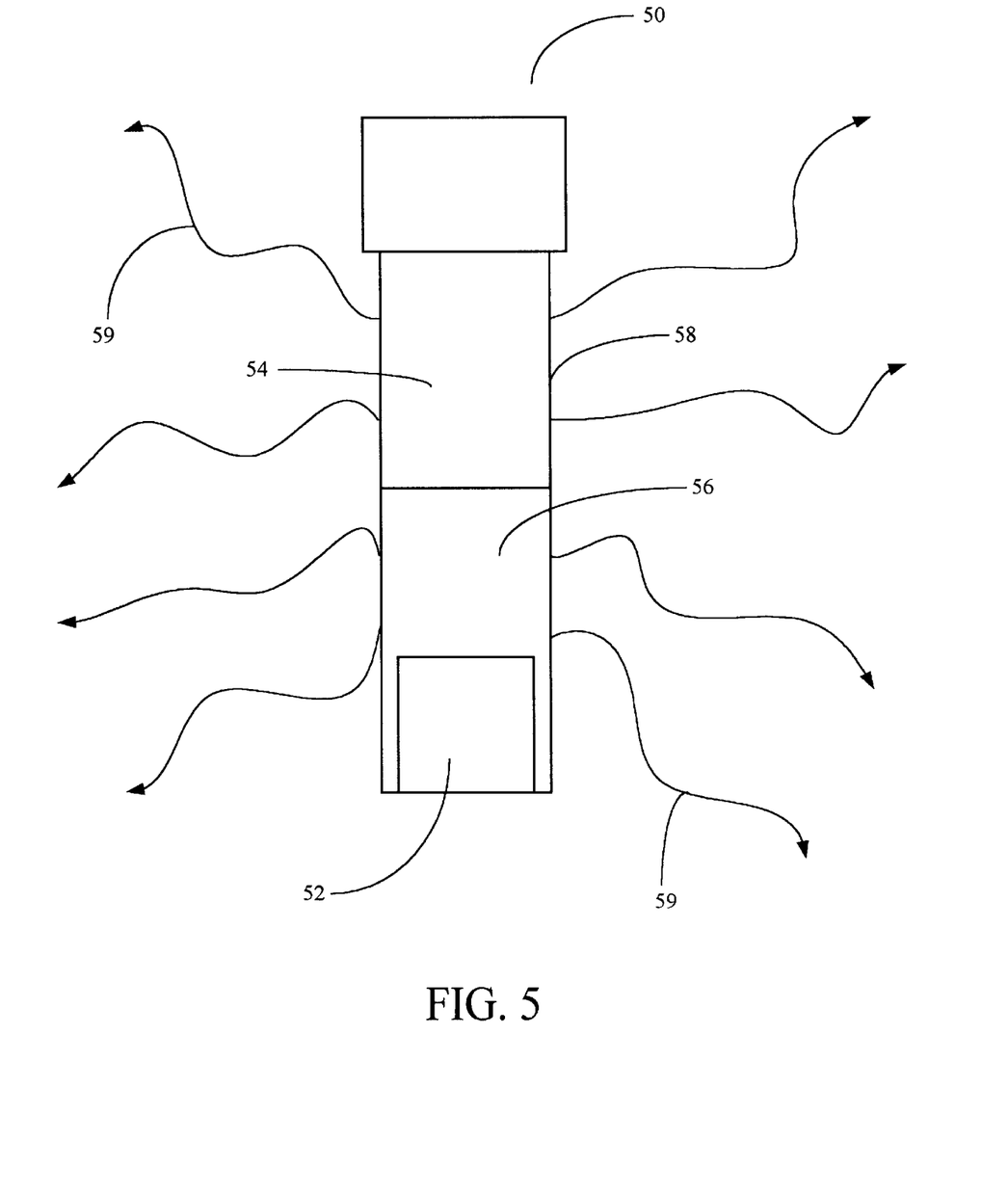
FIG. 5 is an illustration of the permeation tube of a preferred embodiment of the present invention.

The mercury calibration scheme for the multimetals CEMS involves the introduction of mercury vapor 120 into a carrier stream 121, in which the mercury vapor 120 is entrained in the carrier stream 121. A source of mercury vapor 11 entrains the mercury vapor 120 in a carrier stream 121. In a preferred embodiment of the present invention, the source of mercury vapor 11 is a device known commonly as a permeation tube 50, as illustrated FIGS. 1 and 5. Referring to FIG. 5, a permeation tube 50, by definition, is a small container filled with a liquid of a specific substance that has an appreciable vapor pressure at a particular temperature. Consequently, the permeation tube 50 contains a pure chemical compound, e.g. mercury, in a two-phase equilibrium between its liquid 56 and its gas phase 54. An impermeable plug 52 holds the compound in the permeation tube 50. The container 58 is partially constructed using a material that is permeable to the chemical vapor 59 in question. The absolute permeability of the material is a direct function of the temperature of the system, which results in the higher the temperature, the higher the rate of permeation. Referring to FIG. 1, typically, the source of mercury vapor 11 is housed within a constant temperature chamber 10 that can be controlled to within one-tenth of one degree Celsius. In a preferred embodiment of the present invention, an acceptable temperature range for the constant temperature chamber 10 is from about 80° C. to about 110° C. and a most preferable temperature is about 100° C., or the temperature at which the output of the permeation tube has been certified. Temperature control is absolutely essential to achieving a constant and reproducible permeation rate for the chemical vapor in question. The temperature used depends on the desired rate of permeation and also the relative volatility of the liquid source material. The permeation tube 50 also requires a fixed flow of carrier gas through the constant temperature chamber 10 to entrain the permeated chemical vapor and present it to an analyzer 15 or other instrumentation. Often, dilution gases are added to achieve a certain final concentration for the chemical species in question.

In a preferred embodiment of the present invention, a mercury permeation tube is used as the source of mercury vapor 11 and a constant temperature chamber 10 are used, as illustrated in FIG. 1. The carrier air 121 is introduced at a constant rate into the constant temperature chamber 10. The source of the carrier air 126 may be an air compressor or a cylinder of compressed air. The pressure of the carrier air supply is adjusted to approximately 20–40 psi using a pressure regulator. The actual flow rate of the carrier air 121 is maintained using a mass flow regulator 12. The source of mercury vapor 11 is certified to produce a mercury vapor output of a known rate, such as 1.988 micrograms per minute, at a given temperature, such as 100.0° C. The source of mercury vapor 11, e.g. the permeation tube, is placed inside the constant temperature chamber 10 and allowed to equilibrate to the desired temperature. As illustrated in FIG. 1, carrier flow 121 is introduced a constant rate and is allowed to constantly flow through the chamber 10 to entrain the mercury vapor 120. In a preferred embodiment of the present invention, the flow rate of the carrier air 121 is between 100 mL/min and 500 mL/min and most preferably, 300 mL/min. In a preferred embodiment, as the carrier air 121 flows through the chamber, a mercury permeation tube 50 is source of mercury vapor 11 and the mercury permeation tube 11, 50 is bathed in the carrier air 121 and the mercury vapor 120 is entrained in the carrier air 121.

As shown in FIG. 1, a 3-way solenoid valve 13 is positioned such that the mercury vapor/carrier air stream 122 could either flow directly to the trap 16 or upon actuation of the valve 13, the mercury vapor/carrier air stream 122 could be diverted to an aerosol mixing device 14 where it could be combined with a flow diluent air 123. Either an air compressor or a cylinder of compressed air provides the source of diluent air 125. The pressure of the diluent air supply is adjusted to approximately 20–40 psi using a pressure regulator. The actual flow rate of the diluent air 123 is maintained using a mass flow regulator 17. When the mercury vapor/carrier air stream 122 is not in use for measurement or calibration purposes, the valve 13 is adjusted to divert the mercury vapor/carrier air stream 122 through a trap 16 to remove the mercury vapor 120 and prevent emission into the atmosphere. In a preferred embodiment of the present invention, the trap 16 is an activated charcoal trap. The flow of diluent air 123 is introduced at a constant rate, such as 15.0 L/min, and combined with the mercury vapor/carrier air stream 122 to produce a total flow 124. In a preferred embodiment of the present invention, the mixing device 14 has at least two inputs 18 and 19, one for the mercury vapor/carrier air 19 and one for the diluent air 18. Any number of inputs may be used, but for simplicity, two are preferred. The optimal flow rate for the diluent air 123 depends on the particular equipment utilized. The total flow 124 is the combination of the flow of the mercury vapor/carrier air stream 122 and the flow of diluent air 123, such as 0.300 L/min plus 15.0 L/min equals 15.3 L/min. In a preferred embodiment of the present invention, a nominal concentration of the diluted air is calculated by dividing the output rate of the mercury permeation tube 50, the source of mercury vapor 11, by total flow 124, such as 1.988/15.3 or 0.130 micrograms per liter or 130 micrograms per cubic meter.

Figure 2:
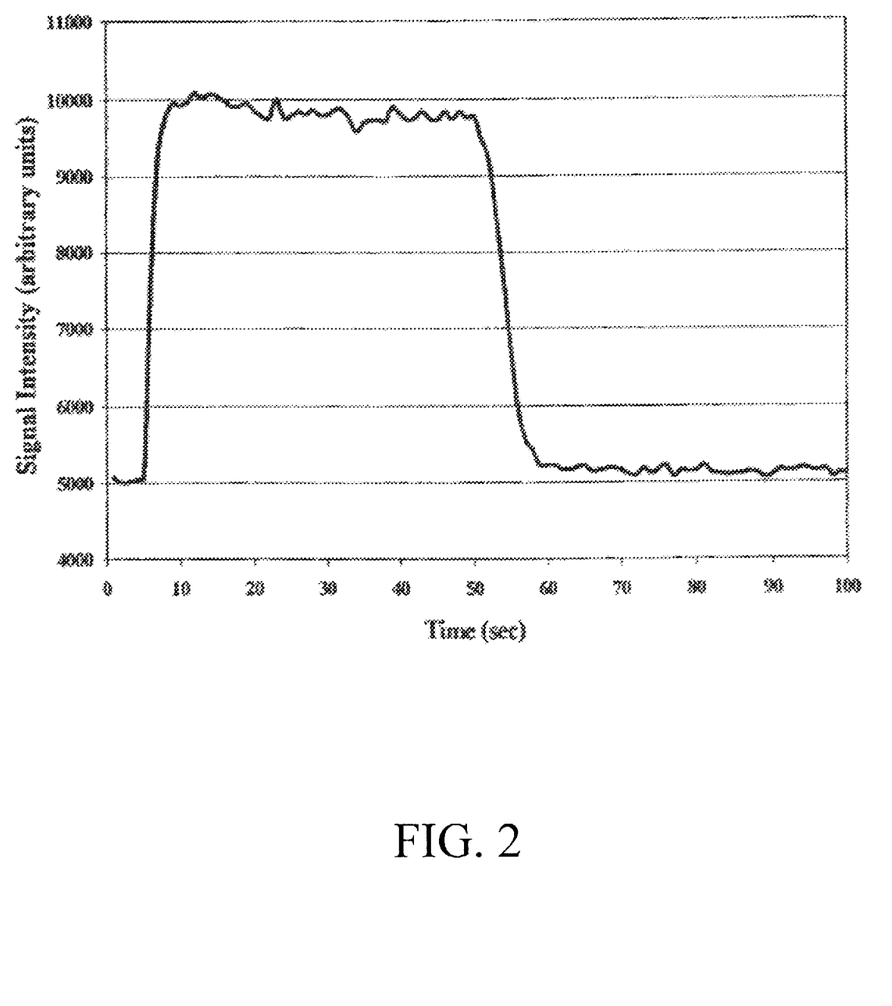
FIG. 2 is a graph of signal intensity vs. time during introduction of sample aliquot containing mercury calibration mixture.

FIG. 2 shows the multimetals CEMS signal response vs. time during introduction of a sample aliquot containing the mercury vapor calibration mixture at a nominal concentration, such as 130 micrograms per cubic meter. The plateau in signal response represents an interval of steady state sample introduction during which an analytical measurement can be made to perform calibration or confirm calibration stability.

Figure 3:
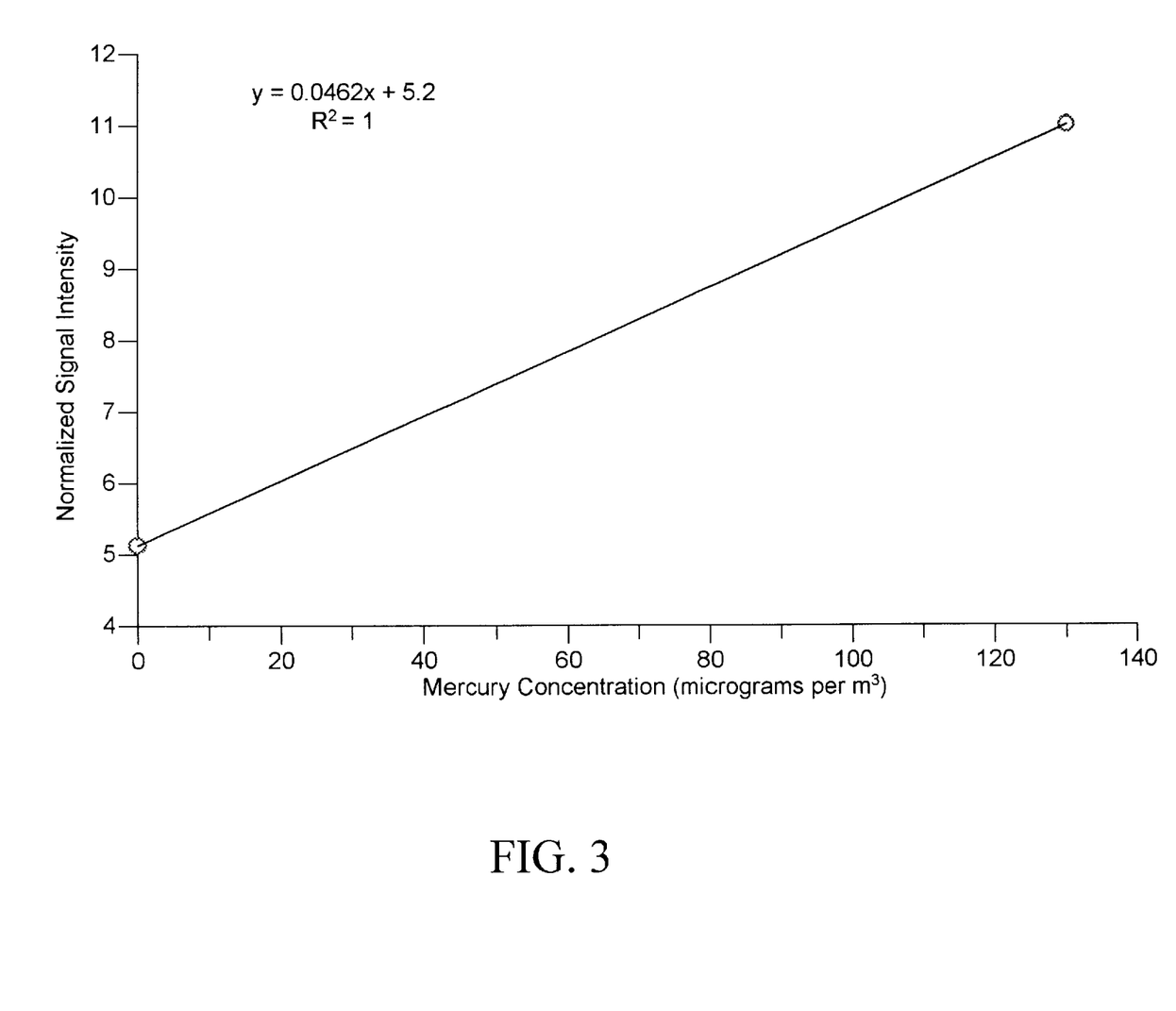
FIG. 3 is a graphical illustration of the linear relationship between signal intensity and mercury concentration given in normalized signal intensity vs. mercury concentration ($\mu g/m^3$).

In a preferred embodiment of the present invention, the multimetals CEMS is calibrated using the following procedure. First, a sample stream of clean air is introduced into the instrument to allow a blank or "Zero" measurement, i.e., in the absence or mercury. A signal intensity is measured in correspondence to the blank sample. However, any known mercury concentration may be used as the source of the second plot, but zero mercury concentration is most preferred because it provides the slope intercept. Next, the 3-way valve controlling the flow of the mercury vapor/carrier air stream is actuated to allow introduction into the instrument. After a 90-second equilibration period, the signal intensity corresponding to the nominal concentration is measured. Using the net signal intensities from the "Zero" and the nominal concentration measurements, a linear relationship between signal intensity and mercury concentration is established, as illustrated in FIG. 3. The linear relationship is the line from the "Zero" measurement to the nominal concentration measurement. This allows for the calibration of the analyzer by adjusting the signal intensity to correspond to a particular known concentration calculated from the slope and slope intercept of the line.

Figure 4:
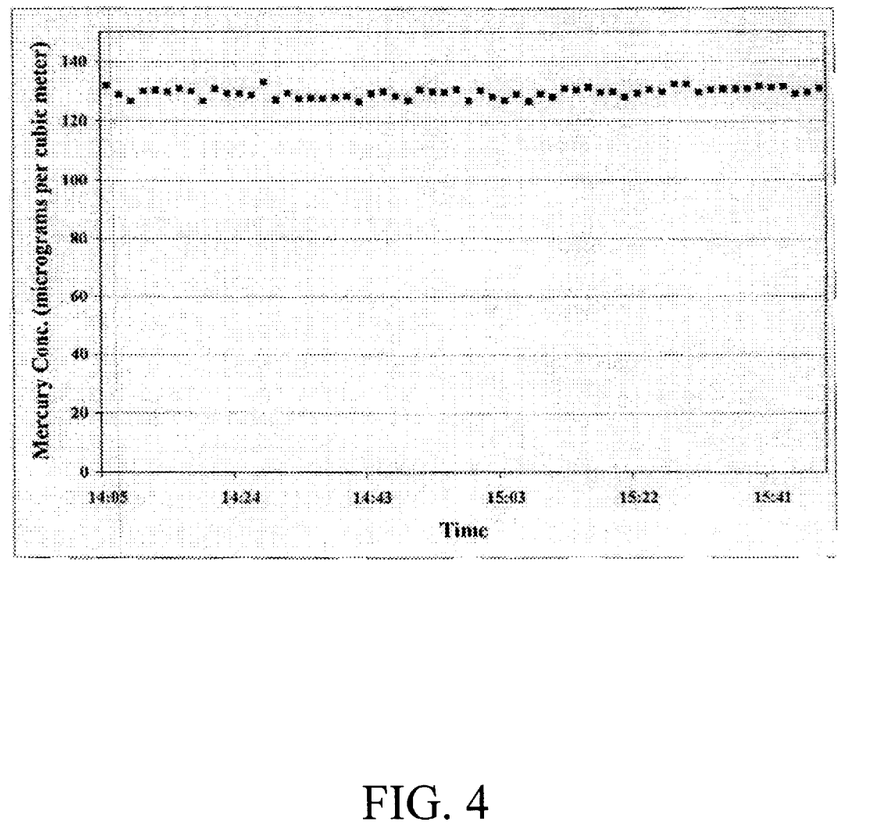
FIG. 4 is a graphical illustration of the short-term stability of the mercury calibration scheme of a preferred embodiment of the present invention given in mercury concentration ($\mu g/m^3$) vs. short-term stability of mercury calibration.

For purposes of quality assurance and quality control, it is customary practice once an analyzer has been calibrated, to confirm the stability of the calibration by re-introducing the original calibration gas or a second gas of known concentration and comparing its measured concentration against a known or certified value. In a preferred embodiment of the present invention, the mercury vapor stream produced by the permeation tube is re-introduced into the multi metal CEMS instrument for that express purpose. FIG. 4 illustrates the short-term stability of the mercury calibration as measured in this manner.

EXAMPLE

Referring to FIGS. 1 and 5, a mercury permeation tube 50 as the source of mercury vapor 11 and a constant temperature chamber 10 were utilized. The mercury permeation tube 50 had an active length of 5.0 cm and was factory-certified to produce a mercury vapor output of 1.988 micrograms per minute at a temperature of 100.0° C. The mercury permeation tube 50 was placed inside the constant temperature chamber 10 and allowed to equilibrate to the desired temperature. Carrier flow 121 of 300 mL/min of air was allowed to constantly flow through the chamber to entrain the mercury vapor 120.

Referring to FIG. 1, the 3-way solenoid valve 13 was positioned such that the mercury vapor/carrier air stream 122 was diverted to the mixing device 14 where it was combined with a flow of diluent air 123. The flow of diluent air 123 was 15.0 L/min and when combined with the mercury vapor/carrier air stream 122, the total flow 124 was 15.3 L/min. At the certified mercury output rate of 1.988 micrograms per minute, the diluted mixture had a nominal concentration of 1.988/15.3 or 0.130 micrograms per liter or 130 micrograms per cubic meter.

FIG. 2 shows the multimetals CEMS signal response vs. time during introduction of a sample aliquot containing the mercury vapor calibration mixture at a nominal concentration of 130 micrograms per cubic meter. The plateau in signal response represents an interval of steady state sample introduction during which an analytical measurement can be made to perform calibration or confirm calibration stability.

To confirm the factory-certified mercury output of 1.988 micrograms per minute at 100° C., a test procedure was executed in which mercury vapor was collected over a 30-minute period and later analyzed to determine the total amount collected and the output rate in micrograms per minute. The mercury vapor/carrier air stream was introduced into a glass impinger containing 25 mL of an acidified 10 percent potassium permanganate solution. The potassium permanganate is a strong oxidizing agent and rapidly converts the mercury vapor to an oxidized form that is soluble in acidic aqueous media. The mercury vapor/carrier air stream was allowed to bubble through the permanganate solution for a total of 30 minutes. The permanganate solution was analyzed in a laboratory using emission spectrometry. Based on the total amount of mercury detected in the permanganate solution, it was determined that the output rate of the permeation tube was approximately 2.0 micrograms per minute, in close agreement with the certified value.

The multimetals CEMS was calibrated using the following procedure. First, a sample stream of clean air was introduced into the instrument to allow a blank or "Zero" measurement, i.e., in the absence or mercury. Signal intensity was measured in correspondence to the blank sample. Next, the 3-way valve controlling the flow of the mercury vapor/carrier air stream was actuated to allow introduction into the instrument. After a 90-second equilibration period, the signal intensity corresponding to the 130 micrograms per cubic meter nominal concentration was measured. Using the net signal intensities from the "Zero" and the nominal concentration measurements, a linear relationship between signal intensity and mercury concentration was established, as illustrated in FIG. 3. The slope of the resulting line was 0.0417 and the slope intercept was 5.2. The linear relationship between signal intensity and mercury concentration is illustrated in FIG. 3. For example, if a known concentration of 60 micrograms per cubic meter is measured in the analyzer, the signal intensity should read 7.972. This may be calculated by multiplying 60 by 0.0462 then adding 5.2 or by finding the desired point on the line.

For purposes of quality assurance and quality control, it is customary practice once an analyzer has been calibrated, to confirm the stability of the calibration by re-introducing the original calibration gas or another gas of known concentration and comparing its measured concentration against a known or certified value. The mercury vapor stream produced by the permeation tube was re-introduced into the multi metal CEMS instrument for that express purpose. FIG. 4 illustrates the short-term stability of the mercury calibration as measured in this manner.

Although the description above contains many specificities, these should not be construed as limiting the scope of the invention but as merely providing an illustration of the presently preferred embodiment of the invention. Thus the appended claims and their legal equivalents should determine the scope of this invention.

What is claimed is:

1. A method of calibration for detection of mercury pollutants by a multimetals continuous emissions analyzer having an analyzer signal intensity, wherein said analyzer is a plasma emissions spectrometer, comprising:

placing a source of mercury vapor having a known output rate inside a constant temperature chamber, wherein said source of mercury vapor produces said mercury vapor;

introducing carrier air into said chamber at a first constant rate, wherein said source of mercury vapor entrains said mercury vapor into said carrier air;

introducing said carrier air into an aerosol mixing device at said first constant rate;

introducing diluent air into said mixing device at a second constant rate;

producing a gaseous mixture having a calibration mercury concentration;

introducing said gaseous mixture into said analyzer;

recording a first signal intensity from said analyzer, wherein said first signal intensity is responsive to said calibration mercury concentration of said gaseous mixture;

plotting a first plot on a graph having coordinates of analyzer signal intensity vs mercury concentration, wherein said first plot is said first signal intensity vs said calibration mercury concentration;

recording a second signal intensity from said analyzer, wherein said second signal intensity is responsive a first known mercury concentration;

plotting a second plot on said graph, wherein said second plot is said second signal intensity vs said first known mercury concentration;

creating a linear relationship between said analyzer signal intensity and said mercury concentration on said graph, wherein said linear relationship is a line, having a slope intercept and a slope, from said first plot to said second plot;

introducing a second known mercury concentration into said analyzer;

calculating a calibration signal intensity from said slope and said slope intercept; and adjusting said analyzer signal intensity to correspond to said calibration signal intensity.

2. The method of claim 1, wherein said constant temperature chamber maintains a temperature of about 80° C. to about 110° C.

3. The method of claim 1, wherein said constant temperature chamber maintains a temperature equal to a certified temperature for said output rate.

4. The method of claim 1, wherein said first constant rate is about 100 mL/min to about 500 mL/min.

5. The method of claim 1, wherein said first constant rate is about 300 mL/min.

6. The method of claim 1, further comprising calculating said calibration mercury concentration by dividing said output rate by an addition of said first and second constant rates.

7. The method of claim 1, wherein said first known mercury concentration is zero mercury concentration.

8. The method of claim 1, wherein said second known mercury concentration is said calibration mercury concentration.

9. The method of claim 1, wherein said source of mercury vapor is a mercury permeation tube.

10. A calibration system for detection of mercury pollutants by a multimetals continuous emissions analyzer, wherein said analyzer is a plasma emissions spectrometer, comprising:

a constant temperature chamber;

a means for controlling air flow operably coupled to said chamber, wherein said means for controlling air flow introduces carrier air into said chamber at a first constant rate;

a source of mercury vapor having a known output rate set inside said chamber, wherein said source of mercury vapor entrains said mercury vapor into said carrier air;

an aerosol mixer, having at least a first input and a second input, operably coupled to said chamber, wherein said carrier air flows out of said chamber and into said mixer via said first input of said mixer at said first constant rate and wherein said mixer is operably coupled to said analyzer;

a means for controlling diluent air operably coupled to said mixer, wherein said means for controlling diluent air introduces diluent air into said mixer via said mixer second input at a second constant rate and wherein a gaseous mixture having a calibration mercury concentration flows from said mixer into said analyzer at a third constant rate;

a graph having coordinates of analyzer signal intensity vs mercury concentration;

a first signal intensity generated by said analyzer in response to said calibration mercury concentration, wherein said first signal intensity and said calibration mercury concentration base a first plot on said graph;

a second signal intensity generated by said analyzer in response to a first known mercury concentration, wherein said second signal intensity and said first known mercury concentration base a second plot on said graph;

a linear relationship between said analyzer signal intensity and said mercury concentration, wherein said linear relationship is a line, having a slope and a slope intercept, on said graph from said first plot and said second plot; and a second known mercury concentration introduced into said analyzer, wherein a calibration signal intensity is generated by said analyzer in response to said second known mercury concentration and wherein said analyzer signal intensity is adjusted to correspond to said calibration signal intensity.

11. The system of claim 10, wherein said first known mercury concentration is a blank having zero mercury concentration.

12. The system of claim 10, wherein said constant temperature chamber maintains a temperature of about 80° C. to about 110° C.

13. The system of claim 10, wherein said constant temperature chamber maintains a temperature of 100° C.

14. The system of claim 10, wherein said first constant rate is about 100 mL/min to about 500 mL/min.

15. The system of claim 10, wherein said first constant rate is about 300 mL/min.

16. The system of claim 10, wherein said source of mercury vapor is a mercury permeation tube.

17. An apparatus for calibration of a continuous emissions analyzer, wherein said analyzer is a plasma emissions spectrometer and wherein said analyzer is detects mercury pollutants, comprising:

a constant temperature chamber;

a means for controlling air flow in flow communication with said chamber, wherein said means for controlling air flow introduces carrier air into said chamber at a first constant rate;

a means for providing mercury vapor having a known output rate set inside said chamber, wherein said means for providing mercury vapor entrains said mercury vapor into said carrier air;

an aerosol mixer, having at least a first input and a second input, in flow communication with said chamber, wherein said carrier air flows out of said chamber and into said first input of said mixer at said first constant rate and wherein said mixer is in flow communication with said analyzer; and a means for controlling diluent air in flow communication with said mixer, wherein said means for controlling diluent air introduces diluent air into said mixer second input at a second constant rate and wherein a gaseous mixture having a calibration mercury concentration flows from said mixer into said analyzer at a third constant rate;

a graph having coordinates of analyzer signal intensity vs mercury concentration;

a first signal intensity generated by said analyzer in response to said calibration mercury concentration, wherein said first signal intensity and said calibration mercury concentration base a first plot on said graph;

a second signal intensity generated by said analyzer in response to a first known mercury concentration, wherein said second signal intensity and said first known mercury concentration base a second plot on said graph;

a linear relationship between said analyzer signal intensity and said mercury concentration, wherein said linear relationship is a line, having a slope and a slope intercept, on said graph from said first plot and said second plot; and a second known mercury concentration introduced into said analyzer, wherein a calibration signal intensity is generated by said analyzer in response to said second known mercury concentration and wherein said analyzer signal intensity is adjusted to correspond to said calibration signal intensity.

18. The apparatus of claim 17, wherein said means for providing mercury vapor is a mercury permeation tube.

19. The system of claim 17, wherein said constant temperature chamber maintains a temperature of 100° C.

20. The system of claim 17, wherein said first constant rate is about 300 mL/min.

21. The apparatus of claim 17, further comprising a three-way valve having an input, a first output and a second output, located between said chamber and said first input of said mixer, wherein said chamber is in flow communication with said three-way valve input and wherein said three-way valve first output is in flow communication with said first input of said mixer.

22. The apparatus of claim 21, further comprising a mercury vapor trap, wherein said three-way valve second output is in flow communication with said mercury vapor trap.

23. The apparatus of claim 22, wherein said mercury vapor trap is an activated charcoal trap.

24. The system of claim 10, further comprising a three-way valve having an input, a first output and a second output, located between said chamber and said first input of said mixer, wherein said chamber is operably coupled to said three-way valve input and wherein said three-way valve first output is operably coupled to said first input of said mixer.

25. The system of claim 24, further comprising a mercury vapor trap, wherein said three-way valve second output is operably coupled to said mercury vapor trap.

26. The apparatus of claim 25, wherein said mercury vapor trap is an activated charcoal trap.

* * * * *